United States Patent
Ager et al.

(10) Patent No.: US 6,432,074 B1
(45) Date of Patent: Aug. 13, 2002

(54) EXTENSION INDICATORS

(75) Inventors: Colin Ager, Cambridge (GB); Alaric Naiman, Lincoln, MA (US); Mark Priest, Cambridge (GB); Tim Jones, Cambridge (GB); Julian Scarfe, Cambridge (GB); Edward Colby, Hertfordshire (GB)

(73) Assignee: Smith & Nephew plc, London (GB)

( * ) Notice: Subject to any disclaimer, the term of this patent is extended or adjusted under 35 U.S.C. 154(b) by 0 days.

(21) Appl. No.: 09/423,449

(22) PCT Filed: May 11, 1998

(86) PCT No.: PCT/GB98/01344
§ 371 (c)(1),
(2), (4) Date: Jun. 30, 2000

(87) PCT Pub. No.: WO98/51247
PCT Pub. Date: Nov. 19, 1998

(30) Foreign Application Priority Data

May 10, 1997 (GB) ................................................ 9709422
May 10, 1997 (GB) ................................................ 9709423

(51) Int. Cl.$^7$ .................................................. A61F 13/00
(52) U.S. Cl. ........................................... 602/75; 602/76
(58) Field of Search ............................... 602/41–59, 75, 602/76, 79

(56) References Cited

U.S. PATENT DOCUMENTS 4,133,307 A * 1/1979 Ness

* cited by examiner

Primary Examiner—Kim M. Lewis
(74) Attorney, Agent, or Firm—Larson & Taylor, PLC

(57) ABSTRACT

An extension indicator is provided for determining a predetermined extension applied to an extensibly deformable article such as medical bandage used in compression therapy. The indicator includes first (420) and second (430) co-operating members, each adapted to be secured to an extensibly deformable article (440). One of the members is more extensible than the other and each member (420, 430) bears visual indicia (450, 460, 470) which upon extension of the more extensible member, are adapted to align with each other to indicate a predetermined extension of the more extensible member.

7 Claims, 4 Drawing Sheets

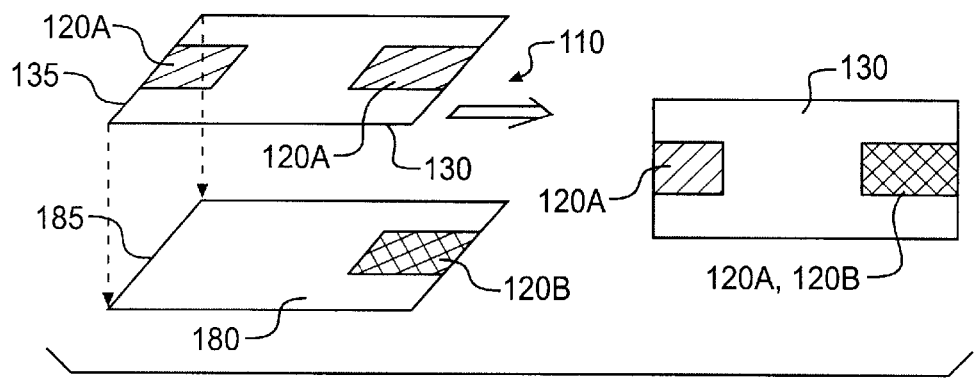
FIG. 1A
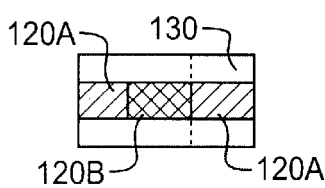 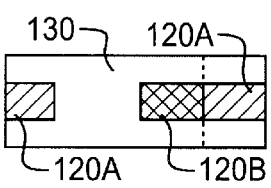 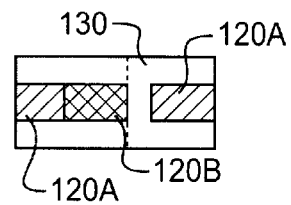
FIG. 1B   FIG. 1C   FIG. 1D
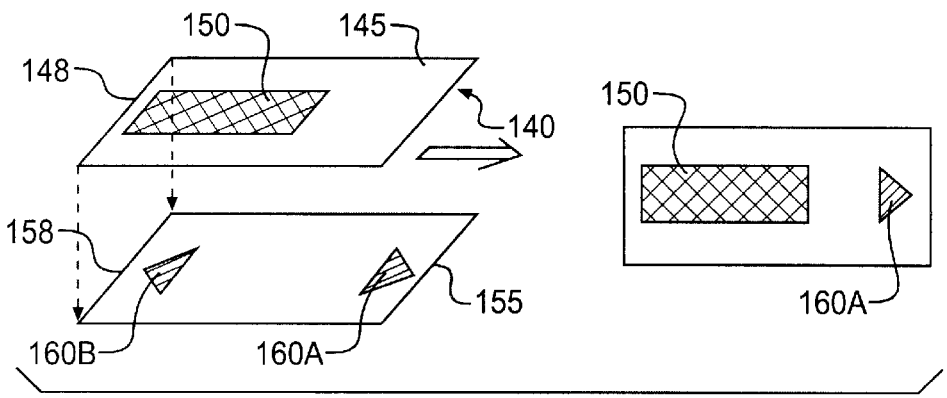
FIG. 1E
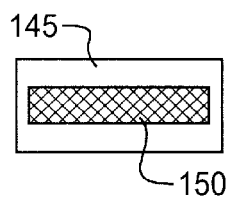 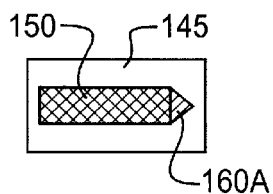 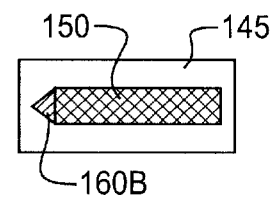
FIG. 1F   FIG. 1G   FIG. 1H

EXTENSION INDICATORS

FIELD OF THE INVENTION

The present invention relates to deformable articles particularly to extensibly deformable articles and to methods for assessing the degree of deformation of such articles visually.

BACKGROUND OF THE INVENTION

For many deformable articles, for example extensible articles it is desirable to be able to assess when a predetermined degree of extension has been achieved. For example it may be desirable to know when a particular material has been extended to a value which is close to its elastic limit in order to avoid exceeding said limit. Such methods are useful in many areas where either an article's extension or the compression or tension it transfers to another object must be known, and where instrumentation is impractical.

In the field of medicine, extensible fabrics are often used in dressings and bandages and if these are applied too tightly to a patient, problems may result due to the high pressure applied. In extreme cases blood flow can be severely impaired and damage to body tissues can result.

For example compression bandages are used primarily in the treatment of leg ulcers where venous insufficiency is a major factor. The compressive forces promote good valve performance in the veins leading to more efficient blood circulation and thus better healing.

However the main perceived difficulty for users of compression bandages is ensuring that enough pressure is applied to a limb to achieve therapeutic benefit without over-tightening the bandage. This often results in under tightening thus greatly reducing any therapeutic benefits.

It is known that figures on the surface of a bandage may act as an indication of the amount of tension. Such a device is disclosed in U.S. Pat. No. 3,613,679.

U.S. Pat. No. 4,133,307 discloses a device where the elastic strip runs within a non-extensible, partly transparent tube where both the strip and tube have markers which when aligned give an indication of the amount of tension.

There is thus a need to provide an effective and convenient way of determining when an extensible article has been extended to a particular degree.

SUMMARY OF THE INVENTION

Therefore in accordance with the present invention there is provided an extension indicator comprising first and second cooperating members, each being adapted to be secured to an extensibly deformable article, in which one of said members is more extensible than the other and in which each member bears visual indication means which upon extension of the more extensible member are adapted to align with each other to indicate a predetermined extension of the more extensible member.

The invention further provides an article comprising an extensible material and including an extension indicator in accordance with the invention and as herein described.

By 'extensible' is meant the ability of the member to be stretched without breaking.

According to a first embodiment of the invention there is provided an extension indicator including at least a first member comprising a transparent extensible layer with a first image present and a second member comprising a layer with a second image present and where the first layer overlays the second layer and the first layer can extend independently relative to the second layer.

Transparency is defined as being able to see through easily and distinctly. Transparency may be achieved by using a transparent material or by cutting slits or holes into an opaque material.

The first and second layers may be connected in such a way that the connection does not impede relative extension of the layers. For example the first layer and the second layer may be connected along a line perpendicular to the axis of extension. Alternatively the first and second layer may be independently bonded to a substrate with no direct connection between layers.

For use as an extension indicator as hereinbefore described the first layer is allowed to extend with respect to the second layer. The images visible on or through the layers change position with relative extension between the layers to indicate extension. On reaching the correct extension the images come into a recognizable alignment, for example the images overlap to give a single image or a single image is positioned between two images.

In one aspect of this first embodiment of the present invention there is provided an extension indicator comprising at least a first transparent extensible layer with a first image present and a second layer with a second image present and a third extendible layer where the first and third layer encapsulate the second layer, and the first layer can extend independently relative to the second layer.

The indicator is aptly at least 0.1 cm long and may be at least 5 cm long (when measured along the length of the indicator prior to the stretching of the fabric). Stretching of the article to a pre-determined extent may cause the indicator to extend for example by at least 10, 50, 100 or 200% for example.

According to a second embodiment of the present invention there is provided an extension indicator comprising at least a first layer wherein the layer contains a slit in the direction of extension, markings on opposite sides and adjacent to the slit and a region of variable elasticity on at least one side of the slit.

For use as an extension indicator as hereinbefore described the indicator is extended and due to the region of variable elasticity on at least one side of the slit, the markings on each side move relative to each other. The correct extension is indicated when the markings line up in a predetermined manner.

Elasticity is the extent to which a material stretches under a given tension.

The extension indicator may comprise at least a first layer where the layer contains a slit in the direction of extension, markings on opposite sides and adjacent to the slit and a region of variable elasticity on at least one side of the slit.

Alternatively the extension indicator may be part of an extensible article in that the article contains a slit in the direction of extension and at least two markings on opposite sides and adjacent to the slit and a region of variable elasticity on at least one side of the slit.

According to a third embodiment of the present invention there is provided an extension indicator comprising at least a first member, for example a layer of material overlaying a second member, for example a second layer of a material wherein the first layer includes an extensible shape with a perforation and the second layer includes an image bearing surface.

For use as an extension indicator in this embodiment of the invention the first layer and the second layer with an image bearing surface are allowed to extend with respect to each other. The image visible through the perforation in the first layer changes with relative extension between the layers to indicate extension. This is achieved by the first layer having a different elasticity to the second layer.

Preferably the first layer has a modulus of elasticity that varies along its length. This can be achieved by having a first layer with a non-uniform shape, for example, a triangle. If a triangle is anchored only at its ends, an applied tension that stretches the triangle will extend the triangle more at the thin end (a single vertex) than at the thick end (a double vertex). Thus when the triangle is fixed to an image bearing surface and the surface is extended, there will be relative movement between the triangle and the surface, thus changing the image visible through a perforation, for example a hole in the triangle.

Preferably the extension indicator comprises a first layer comprising a triangular piece of fabric with a perforation at one end fixed to an image bearing surface. Extension is to be indicated along a longitudinal axis of the image bearing surface. The triangle is fixed to the surface along one edge on a lateral axis, with the perforation in a corner at a point furthest from the fixed edge. The corner is also fixed to the surface. The image bearing surface is provided with markings, the relative position of which to the perforation indicate whether the correct extension has been achieved.

In one aspect of this embodiment a single mark may be provided which coincides with the perforation on the correct extension. In another aspect at least two marks may be provided on each side of where the perforation coincides with the single mark on the correct extension. In this example, when the marks are not visible the correct extension has been achieved.

In accordance with a fourth embodiment of the present invention there is provided an extension indicator for an extensible article wherein said first and second members comprise first and second substantially overlapping strips, each strip being provided with first and second ends, and wherein (i) the first end of the first strip is attached to the extensible article, (ii) the second end of the second strip is attached to the extensible articles (iii) the first strip is substantially transparent and has a first image on it, and the second strip has a second image on it, and, (iv) the second end of the first strip and the first end of the second strip substantially overlap.

For use as an extension indicator as hereinbefore described the two strips are allowed to move with respect to each other. The images visible through the strips change position with relative movement between the strips to indicate extension of the extensible article. On reaching the correct extension the images come into a recognizable alignment, for example the images overlap to give a single image or a single image is positioned between two images.

In order to protect the indicator, the indicator may be provided with an extensible, substantially transparent top layer which may or may not be attached to the indicator.

Furthermore to aid application of the indicator to an article the indicator may be attached to an extensible base layer.

In one aspect of this fourth embodiment of the present invention there is provided an extension indicator for an extensible article comprising at least a first and second substantially overlapping strip, each with a first and second end where (i) the first end of the first strip is attached between an extensible base layer and an extensible, substantially transparent top layer., (ii) the second end of the second strip is attached between the extensible base layer and the extensible, substantially transparent top layer, (iii) the first strip is substantially transparent and has a first image on it and the second strip has a second image on it, (iv) the second end of the first strip and the first end of the second strip substantially overlap, and (v) the extensible base layer is attached to the extensible article.

Desirably the indicator does not substantially impede stretching of the extensible article, ie. the force required to stretch an article to a given degree is not substantially increased by the presence of the indicator.

One or more indicators may be placed at different positions on the article in order to assess the extension at different regions of the article. For example, if indicators are placed at different positions along the length of an extensible article the indicators may indicate the same degree of extension if it desired for the article to be stretched to the same degree along its length or they may indicate different degrees of extension if it is desired for the article to be stretched to the different degrees along its length to provide graduated extension.

The indicator preferably contrasts in color and/or design with the article in order that it can be clearly seen.

Extension indicators in accordance with the invention have many applications but are especially useful in the areas of compression therapy in which the extensible article is an extensible bandage. Such bandages may be used in a method for the treatment of one or more of the following disorders; namely; venous disorders, lymphodoema, which comprises applying a bandage or article according to the invention to the affected site on a patient.

Apart from uses in the medical area the extension indicators of the present invention have applications in other areas such as replacements for conventional force sensors, pressure sense extension indicators, strain indicators and dynamic decorations. A wide range of applications include weigh scales, barometers, exercise equipment, sports equipment, toys, packaging and clothing.

As a weigh scale, the material of the extension indicator is preferably elastic and could provide the spring force directly, providing a light, flexible, collapsible weighing device. An object could be weighed by holding one end of the indicator and fastening the object to the other end. The extension of the indicator could then be calibrated to read directly the weight of the object. This has the advantage of being easy to pack and carry, for example for walking, fishing and hunting.

In another example, the indicator could be fastened in-line with an object to which tension is being applied, and calibrated to display the tension. The large scale, easy-to-read indication would be an advantage in, for example, tensioning sails, tensioning guy ropes for tents or other structures, tensioning bows for archery, or tensioning strings on musical instruments.

In a further example, the indicator is attached across an object, the extension of which is to be indicated. As the indicator is light in weight and conformable, it is particularly suited as an indicator to show correct inflation of inflatable objects such as footballs, boats, or tires. Similarly, the indicator could be used to show how a material is stretched over an object. For example, if attached to the extendible clothing, it could be used to give a direct visual read-out of a person's measurements. In this application, the conformability and the softness of the indicator are major advantages, along with light weight and ease of reading. Another advantage is that the extension indication is positioned directly on the surface of the object concerned, so the user does not have to look away to a separate gauge.

In the case where the extensible article is a bandage the indicator may be located centrally or along an edge of a article. If more than one indicator is provided these may be located together or separately to enhance visibility on application of the article, for example in bandage form, to a patient.

BRIEF DESCRIPTION OF THE DRAWINGS

The present invention will be exemplified with reference to the accompanying drawings and in the following Examples.

FIGS. 1A to 1H illustrate the first embodiment of the invention, wherein:

FIG. 1A shows a schematic view of an unextended extension indicator with the two layers separated for clarity, and a schematic view of the appearance thereof.

FIG. 1B shows a schematic view of the appearance of an extension indicator where the indicator is extended to the required extension.

FIG. 1C shows a schematic view of the appearance of an extension indicator where the indicator is extended less than the required extension of its length.

FIG. 1D shows a schematic view of the appearance of an extension indicator where the indicator is extended more than the required extension of its length.

FIG. 1E shows a schematic view of an unextended extension indicator of another aspect of the first embodiment with the two layers separated for clarity, and a schematic view of the appearance thereof.

FIG. 1F shows a schematic view of the appearance of an extension indicator shown in FIG. 1E where the indicator is extended to the required extension.

FIG. 1G shows a schematic view of the appearance of an extension indicator of the aspect shown in FIG. 1E where the indicator is extended less than the required extension of it's length.

FIG. 1H shows a schematic view of the appearance of an extension indicator of the aspect shown in FIG. 1E where the indicator is extended more than the required extension of its length.

FIGS. 2A to 2D illustrate the second embodiment of the invention wherein:

FIG. 2A shows a schematic view of an unextended article with an extension indicator in accordance with this embodiment.

FIG. 2B shows a schematic view of an article with an extension indicator where the indicator is stretched to the required extension of its length.

FIG. 2C shows a schematic view of an article with an extension indicator where the indicator is stretched less than the required extension.

FIG. 2D shows a schematic view of an article with an extension indicator where the indicator is stretched more than the required extension.

FIGS. 3A to 3D illustrate the third embodiment of the invention wherein:

FIG. 3A shows a schematic view of an article with an extension indicator, with the two layers separated for clarity.

FIG. 3B shows a schematic view of an article with an extension indicator where the article is stretched to the required extension of its length.

FIG. 3C shows a schematic cross-section view of an article with an extension indicator where the article is stretched less than the required extension.

FIG. 3D shows a schematic cross-sectional view of an article with an extension indicator where the article is stretched more than the required extension.

FIGS. 4A to 4C illustrate the fourth embodiment of the invention wherein:

FIG. 4A shows a schematic view of an unextended extension indicator with the two strips separated for clarity, and a top plan view of the appearance.

FIG. 4B shows a schematic view of an extended extension indicator where the indicator is extended to the required extension with the two strips separated for clarity, and a top plan view of the appearance.

FIG. 4C shows a cross-sectional where the indicator is not extended and the indicator is encapsulated between two extensible layers.

DESCRIPTION OF THE PREFERRED EMBODIMENTS

EXAMPLE 1

(FIGS. 1A to 1H)

Figure 2A:
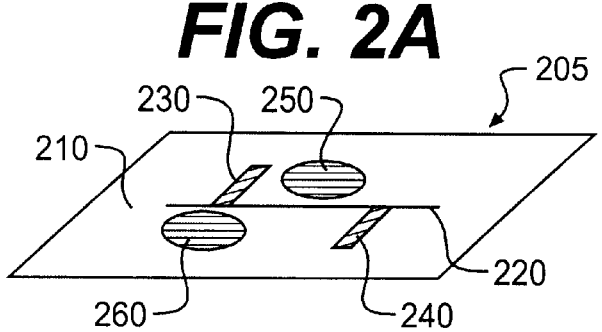

Referring now to FIG. 1A, an extension indicator 110 with a first layer 130 with a first rectangular image 120A and a second layer 180 with a second image 120B is shown schematically. First layer 130 is attached at first end 135 to first end 185 of second layer 180.

The extension indicator. 110 is unextended and the images 120A, 120B visually appear as two separate images.

In FIG. 1B the extension indicator has been extended by the required amount so that the two images 120A, 120B connect exactly. In this example the visual appearance is of a single image.

In FIGS. 1C and 1D the extension indicator 110 is extended relatively to the required amount. In FIG. 1C the indicator 110 is not extended enough and in FIG. 1D the indicator 110 is extended too far.

In these examples the visual appearance is of two images with a varying degree of spacing according to the degree of extension.

Referring now to FIG. 1E an extension indicator 140 with a first layer 145 with a first rectangular image 150 and second layer 155 with a first triangular image 160A and a second triangular image 160B is shown schematically, with the two layers separated for clarity. First layer 145 is attached at first end 148 to first end 158 of second layer 155.

The extension indicator 140 is unextended and the images 150 and 160A visually appear as two separate images. The direction of the triangle indicates the direction in which extension is required.

In FIG. 1F the extension indicator 140 is extended by the required amount to that image 150 overlaps images 160A and 160B. In this example the visual appearance is of a single image.

In FIGS. 1G and 1H the extension indicator 40 is extended relatively to the required amount. In FIG. 1G the indicator 140 is not extended enough and in FIG. 1H the indicator 140 is extended too far.

In these examples the visual appearance is of two images with a varying degree of spacing between the images. Furthermore the direction of the triangle indicates whether extension or relaxation is required.

In a practical application of the first embodiment of the invention an extension indicator(140) may be formed from two layers (145,155—FIG. 1E) of material where the first layer (145) is transparent and is made from, for example polyurethane or natural rubber. The first layer (145) is more extensible than the second layer (155) and which is made from, for example polyester. An image, for example a rectangle is printed on the more extensible layer (145) and an image, for example two triangles pointing in opposite directions is printed on the less extensible second layer (155). Layer 145 is placed on top of the second layer and the two layers are joined along one edge to the bandage. The opposite edge of the first layer is also joined to the bandage such that when the bandage is stretched to the correct extension the images overlap completely. Thus the bandage constitutes a third extensible layer and the second layer (155) is encapsulated between the first layer (145) and this third layer.

EXAMPLE 2
(FIGS. 2A to 2D)

Referring now to FIG. 2A, an elastic article 205 with an extension indicator 210 is shown schematically. The indicator 210 comprises a slit 220, two markings 230, 240 and two regions of reduced elasticity 250, 260.

Figure 2B:
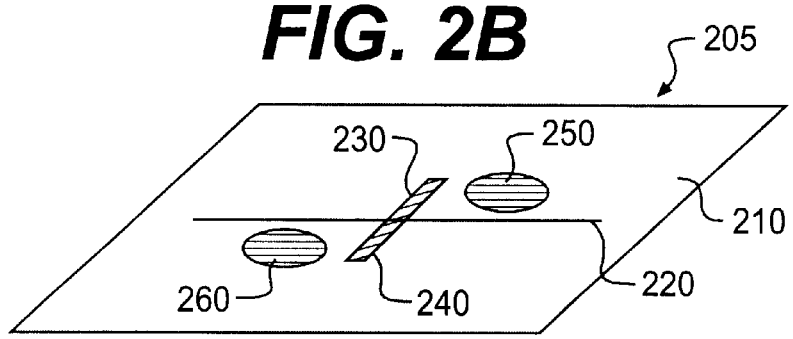

In FIG. 2B the indicator 10 has been extended by the required amount so that the markings 230, 240 on each side of the slit 220 line up.

Figure 2C:
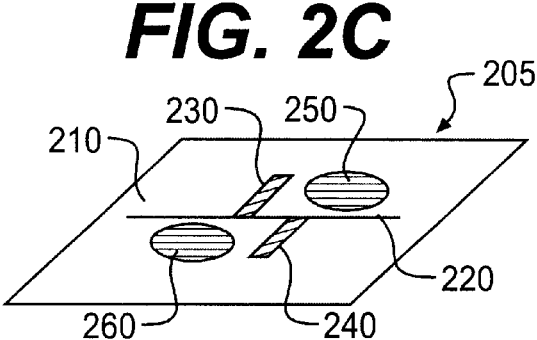
Figure 2D:
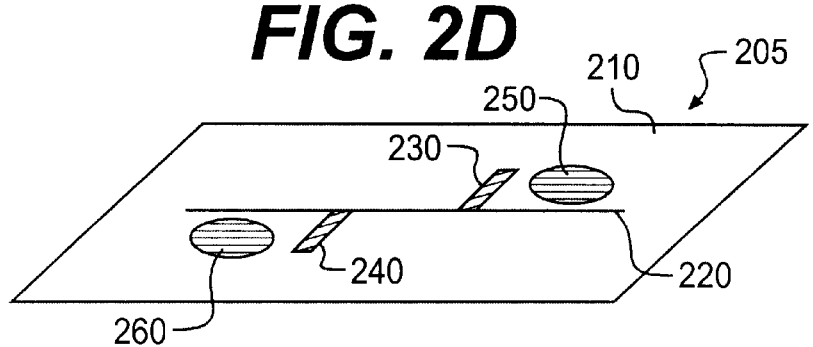

In FIGS. 2C and 2D the indicator 210 is stretched relatively to the required amount. In FIG. 2C the indicator is not stretched far enough and in FIG. 2D the indicator is stretched too far.

In these examples the visual appearance of the extension indicator is that the markings do not line up.

In a practical application of the second embodiment of the invention a 5 cm slit (220)is cut along the longitudinal axis of an elastic bandage (205). At one end of the slit, on one side is added a patch of latex (250) approximately 1 cm². An equivalent patch (260) is added at the opposite end on the opposing side of the slit. The latex is left to cure. The bandage is subsequently stretched by 50%, which in this example is the required amount, and a substantially perpendicular mark (230, 240) is made across the slit, half way along the slit.

The procedure is repeated at 20 cm intervals.

The bandage is allowed to relax and is rolled up ready for use.

EXAMPLE 3
(FIGS. 3A to 3D)

Figure 3A:
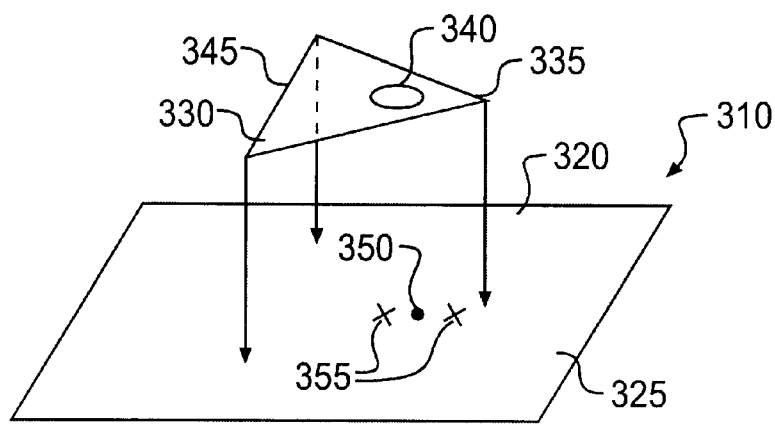

Referring now to FIG. 3A, article 310 with an extension indicator 320 comprising a triangular piece of material 330 and an image bearing surface 325, with images 350, 355, is shown schematically.

The indicator 320, is set up so that the perforation 340 allows viewing of the article surface 325. The triangle 330 is fixed to the surface 325 at the vertex 335 and along edge 345.

Figure 3B:
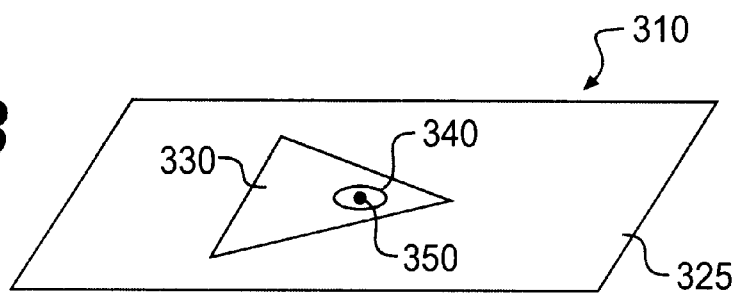

In FIG. 3B the article 310 has been extended by the required amount so that the perforation 340 falls on an image 350. In this example the visual appearance of the extension indicator is of a single dot 350 visible through the perforation.

Figure 3C:
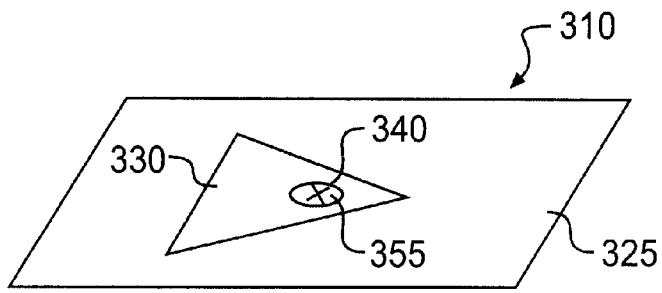
Figure 3D:
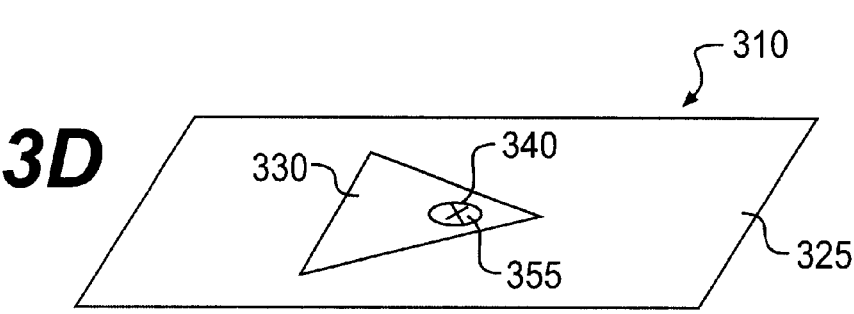

In FIGS. 3C and 3D the article 310 is stretched relatively to the required amount. In FIG. 3C the article 310 is not stretched far enough and in FIG. 3D the article 310 is stretched too far.

In these examples the visual appearance is a cross 355 showing through the perforation 340 indicating that the extension is incorrect.

In a practical application of this embodiment a triangular piece of fabric (330) has a hole (340) punched out at one vertex (335) and is fixed along the opposite edge (345) and at the vertex to an elastic bandage, so that the fixed edge is along the lateral axis. The bandage is extended by the required amount, in this case 50% and a mark (350) is made on the bandage through the hole in the vertex.

The procedure is repeated along the length of the bandage at 20 cm intervals.

Figure 4A:
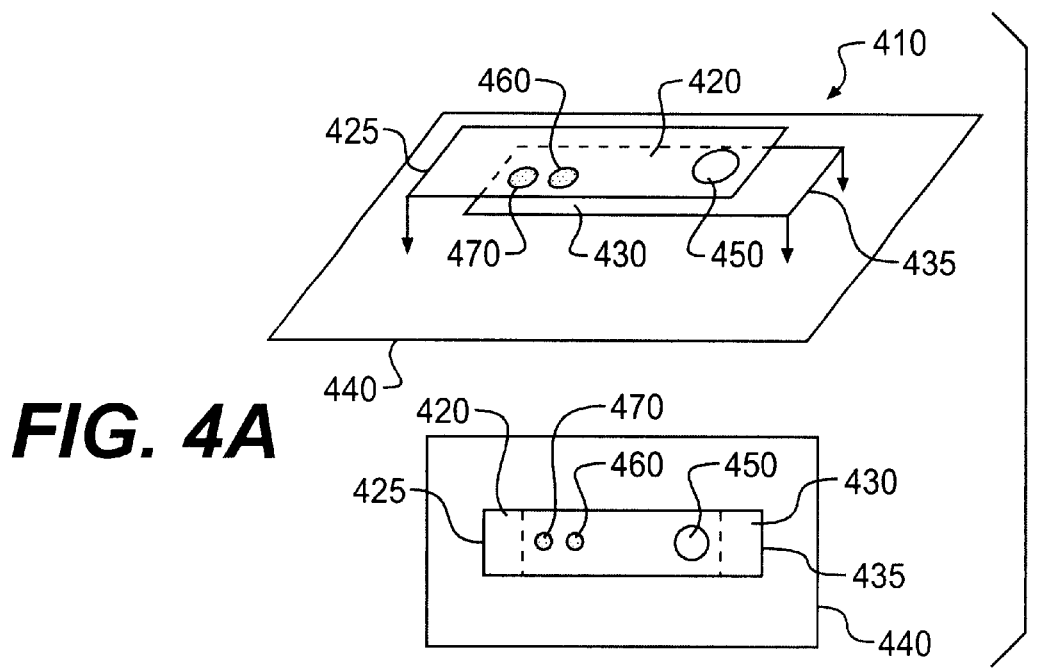
Figure 4B:
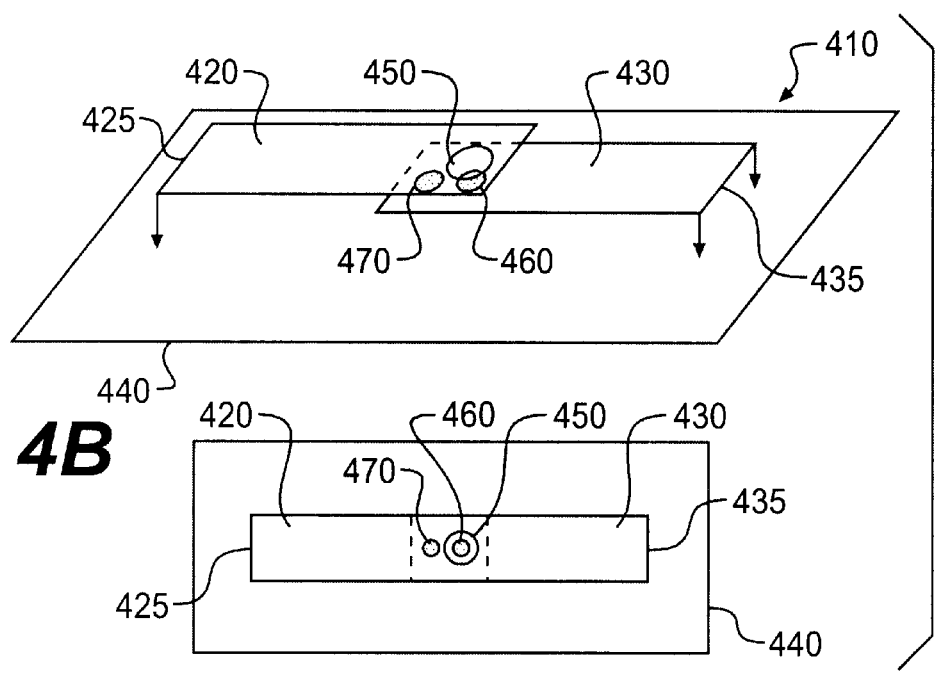
Figure 4C:
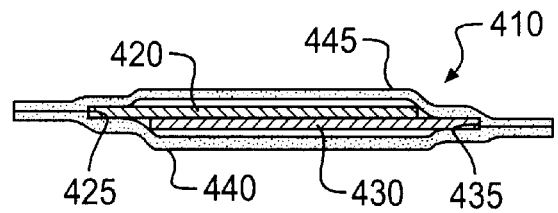

EXAMPLE 4
(FIGS. 4A to 4C)

Referring now to FIG. 4A, an extension indicator 410 with a first strip 420 and a second strip 430 is shown schematically. First strip 420 is attached at first end 425 to an extensible base layer 440 and second strip 430 is attached at second end 435 to the extensible base layer 440. First strip 420 is transparent and is provided with an image 450 comprising a circular ring.

Second strip 430 is provided with two circular images 460 and 470 at a set distance apart, to indicate 50% and 75% extension respectively.

The extension indicator is unextended and the images visually appear in a top plan view as three separate images.

In FIG. 4B the extension indicator of FIG. 4A has been extended by 50% so that image 450 exactly overlaps image 460. In this example the visual appearance, in a top plan view is of two images.

In FIG. 4C a cross-sectional view of an embodiment of the invention is shown unextended.

First strip 420 and second strip 430 are encapsulated within an extensible base layer 440 and an extensible transparent top layer 445, wherein the first end 425 of first strip 420 is attached between layer 440 and layer 445 and the second end 435 of second strip 430 is attached between layer 440 and layer 445.

In a practical application of this embodiment an extension indicator (410) may be prepared by printing up two strips (420, 430) of inextensible transparent polyester with images, such as a ring (450) on the first strip and two filled circles (460) on the second strip. The strips are overlapped substantially on an extensible polyurethane base layer (440) such that the first end (425) of the first strip (420) and the second end (435) of the second strip (430) are in direct contact with the base layer. A transparent extensible polyurethane top layer (445) is overlaid on top of the strips and the two layers are RF (radio frequency) welded together so that that first end of the first strip and the second end of the second strip is attached to both layers and the remaining length of the strips are encapsulated between the layers and are free to move relative to each other on extension of the layers.

The bandage is allowed to relax and is rolled up for use.

What is claimed is:

1. An extension indicator comprising extensible first and second co-operating members in which one of said members is more extensible than the other and in which each member bears visual indication means which upon extension of the more extensible member are adapted to align with each other to indicate a predetermined extension of the more extensible member, the first member comprising a first transparent extensible layer with a first image present and the second member comprising a second layer with a second image present and the first layer overlaying the second layer and the first layer being extensible independently relative to the second layer.

2. The indicator as claimed in claim 1 in which a third extensible layer is provided wherein the first layer and third layer encapsulate the second layer.

3. An extension indicator comprising extensible first and second co-operating members in which one of said members is more extensible than the other and in which each member bears visual indication means which upon extension of the more extensible member are adapted to align with each other to indicate a predetermined extension of the more extensible member, the first and second members being on opposite sides of a layer substantially separated by a slit in the layer, the layer having a direction of extension, the slit extending in the direction of extension, and said visual indication means are markings on the first and second members on opposite sides of and adjacent to the slit, at least one of said members being defined by a region of variable elasticity on one side of the slit.

4. An extension indicator comprising extensible first and second co-operating members in which one of said members is more extensible than the other and in which each member bears visual indication means which upon extension of the more extensible member are adapted to align with each other to indicate a predetermined extension of the more extensible member, said first member overlaying said second member, and the first member including an extensible component defining a shaped form with a perforation therein and the second member including an image bearing surface.

5. The indicator as claimed in claim 4 wherein the component is triangular in shape and is attached to the first member at a vertex and opposite edge, said component having a line of extension and said vertex and edge being aligned along the line of extension of the component.

6. An extension indicator comprising extensible first and second co-operating members in which one of said members is more extensible than the other and in which each member bears visual indication means which upon extension of the more extensible member are adapted to align with each other to indicate a predetermined extension of the more extensible member, said first and second members comprising first and second substantially overlapping strips, each strip being provided with first and second ends, and (i) the first end of the first strip being adapted to be attached to an extensible article, (ii) the second end of the second strip being adapted to be attached to the extensible article, (iii) the first strip being substantially transparent and having a first image on it, and the second strip having a second image on it, and (iv) the second end of the first strip substantially overlapping the first end of the second strip.

7. An extension indicator comprising extensible first and second co-operating overlapping layers in which one of said layers is more extensible than the other and in which each layer bears visual indication means which, upon extension of the more extensible layer, are adapted to align with each other to indicate a predetermined extension of the more extensible layer.

* * * * *